(12) United States Patent
Van Essen

(10) Patent No.: US 8,578,940 B1
(45) Date of Patent: Nov. 12, 2013

(54) ATHLETIC MOUTH GUARD

(75) Inventor: Robert Dean Van Essen, Hudsonville, MI (US)

(73) Assignee: Robert D. Van Essen, DDS, PC, Hudsonville, MI (US)

( * ) Notice: Subject to any disclaimer, the term of this patent is extended or adjusted under 35 U.S.C. 154(b) by 101 days.

(21) Appl. No.: 13/179,865

(22) Filed: Jul. 11, 2011

Related U.S. Application Data

(63) Continuation-in-part of application No. 12/454,199, filed on May 14, 2009, now abandoned.

(60) Provisional application No. 61/155,639, filed on Mar. 16, 2009.

(51) Int. Cl.
*A61C 5/14* (2006.01)
(52) U.S. Cl.
USPC .......................... 128/859; 128/861
(58) Field of Classification Search
USPC ............... 128/859, 861–862; 602/902; 433/6
See application file for complete search history.

(56) References Cited

U.S. PATENT DOCUMENTS 4,114,614 A * 9/1978 Kesling ................. 128/861
6,055,986 A * 5/2000 Meade ................... 128/848

* cited by examiner

*Primary Examiner* — Patricia Bianco
*Assistant Examiner* — Camtu Nguyen
(74) *Attorney, Agent, or Firm* — The Watson I.P. Group; John N. Jovanovic; Vladan M. Vasiljevic

(57) ABSTRACT

An athletic mouth guard comprising an upper component a lower component and first and second joining components. The upper component has a central region and first and second opposing wing regions. These cooperate to define a channel-like configuration which is structurally configured to receive a plurality of teeth of an upper jaw. The lower component has similar structures which are configured to receive a plurality of teeth of a lower jaw. The first joining component is attached to the upper component and to the lower component along corresponding first opposing wing regions and the second joining component is attached to the upper component and to the lower component along corresponding second opposing wing regions. The joining components fix the portions of the wing regions to the respective first and second joining component, and to each other, in a spaced apart orientation, such that placement of the same in a mouth of a user directs a lower jaw of a mouth of a user to move forward relative to a position thereof in a habitual closure.

12 Claims, 4 Drawing Sheets

ATHLETIC MOUTH GUARD

CROSS-REFERENCE TO RELATED APPLICATION

The present application is a continuation-in-part of U.S. patent application Ser. No. 12/454,199 entitled "A dual laminated mouth guard for both maxillary and mandibular jaws that is connected in a fashion to advance the jaw forward for better air flow through the mouth and to protect the jaws" which was filed on May 14, 2009 now abandoned, which claims priority from U.S. Prov. Pat. App. Ser. No. 61/155,639 filed Mar. 16, 2009, the entire specification of both applications is hereby incorporated herein by reference.

BACKGROUND OF THE DISCLOSURE

1. Field of the Disclosure

The disclosure relates in general to athletic mouth guards, and more particularly, to an athletic mouth guard that provides impact protection (to lessen concussions and the severity of concussions), while providing protection to a user and while facilitating the opening of the airway passages.

2. Background Art

The use of mouth guards is well known. One particular class of mouth guards is configured for use in sports. Sports such as basketball, football and lacrosse, among others (typically, contact sports) expose players to mouth injuries received from direct impacts from outside objects. Many of these mouth guards include a single component which comprises a pair of spaced apart walls and a base which together define a cavity into which the upper teeth are directed. Generally, the user utilizes heat to soften the mouth guard and then places the mouth guard into his or her mouth. By pressing down on the mouth guard with the user's teeth, the impressions of the teeth are made into the inner surface of the channel of the mouth guard. Thus, a custom fit is provided. The mouth guard tends to preclude the biting of the tongue inadvertently, or chipping teeth through tooth to tooth contact between the lower jaw and the upper jaw.

Other mouth guards have a base with opposing spaced apart walls that extend above and below the base thereby defining two opposing channels. One of the channels is intended for the upper teeth and one of the channels is intended for the lower teeth. The user utilizes the same procedure to imprint the teeth into the surface of the channel. Typically such a configuration is utilized in football applications, although not limited thereto.

Problematically, these mouth guards perform a single function which is to limit dental injuries to the user. Thus, they are typically formed from a thermoplastic material which is easily deformable under mild heat, and which is generally injection molded from a single polymer. At times, a stronger base polymer is provided and a softer polymer is coupled thereto so that the imprint of the teeth can be made into the softer material. The harder material is configured to preclude deformation.

The mouth guards typically force the player's mouth to be closed or nearly closed to insure the proper positioning thereof. Additionally, these mouth guards are made from materials that do little to dissipate hits to the lower jaw. Additionally, they provide little protection to direct impact, as they are positioned on the upper jaw and have nothing to do with the lower jaw.

It would be helpful if a mouth guard provided enhanced breathing, as well as tooth protection, while directing the lower jaw into a position relative to the upper jaw that would greatly minimize and dissipate an impact so as to minimize the effect thereof on the skull (and in turn, brain) of the player. Such dissipation of an impact being achieved through the proper selection of material and also through the proper positioning of the lower jaw relative to the upper jaw.

It is therefore an object of the present invention to protect the player, or user, from dental injuries.

It is another object of the present invention to dissipate impact that is imparted onto the mouth guard through the formation of the mouth guard components.

It is another object of the invention to dissipate impact that is imparted onto the mouth guard so as not to direct it to the skull of the user, through the movement of the lower jaw relative to the upper jaw in a position so that the lower jaw is moved forward of its position in the habitual closure.

These objects as well as other objects of the present invention will become apparent in light of the present specification, claims, and drawings.

SUMMARY OF THE DISCLOSURE

The disclosure is directed to an athletic mouth guard comprising an upper component, a lower component and first and second joining components. The upper component has a central region and first and second opposing wing regions. These cooperate to define a channel-like configuration which is structurally configured to receive a plurality of teeth of an upper jaw. The lower component has similar structures which are configured to receive a plurality of teeth of a lower jaw. The first joining component is attached to the upper component and to the lower component along corresponding first opposing wing regions and the second joining component is attached to the upper component and to the lower component along corresponding second opposing wing regions. The joining components fix the portions of the wing regions to the respective first and second joining component, and to each other, in a spaced apart orientation, such that placement of the same in a mouth of a user directs a lower jaw of a mouth of a user to move forward relative to a position thereof in a habitual closure.

In a preferred embodiment, the upper component comprises a plurality of layers of elastically deformable thermoplastic material.

In one such preferred embodiment, the plurality of layers comprises at least four layers.

In another preferred embodiment, the lower component comprises a plurality of layers of elastically deformable thermoplastic material.

Preferably, the upper component and the lower component are one of substantially parallel to each other, and, angled relative to each other so as to increasingly separate away from the first and second joining components.

In another such preferred embodiment, the upper component are angled relative to each other at an angle $\alpha$, which is between 0 and 40 degrees.

In a preferred embodiment, the athletic mouth guard further includes a first joining cap member extending over and attached to a portion of the upper component, the lower component and the first joining component, to, in turn, provide enhanced strength thereto. Further the athletic mouth guard includes a second joining cap member extending over and attached to a portion of the upper component, lower component and the second joining component, to, in turn, provide enhanced strength thereto.

Preferably, the upper and the lower components include four layers each, which layers include ethylene vinyl acetate (EVA).

BRIEF DESCRIPTION OF THE DRAWINGS

The disclosure will now be described with reference to the drawings wherein.

DETAILED DESCRIPTION OF THE DISCLOSURE

Figure 1:
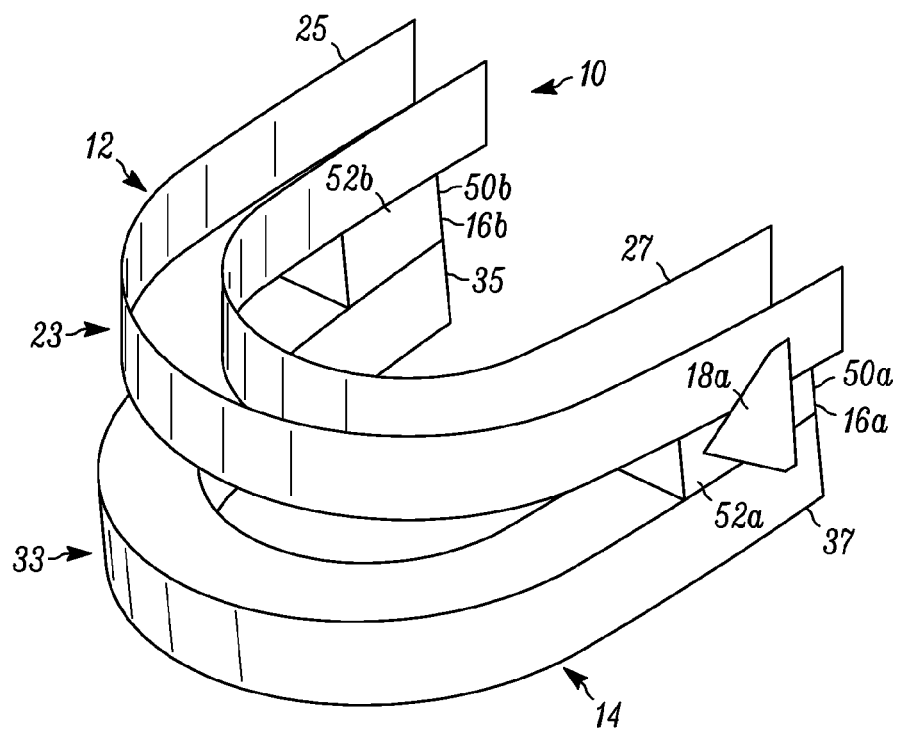
FIG. 1 of the drawings is a perspective view of the athletic mouth guard of the present disclosure.

While this invention is susceptible of embodiment in many different forms, there is shown in the drawings and described herein in detail a specific embodiment with the understanding that the present disclosure is to be considered as an exemplification and is not intended to be limited to the embodiment illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Referring now to the drawings and in particular to FIG. 1, the athletic mouth guard is shown generally at 10. The mouth guard is configured and particularly well suited for athletics. Advantageously, the mouth guard is configured to protect the user from concussions, while protecting the teeth and the mouth. In addition, the configuration facilitates the opening of the passage to improve respiration for the user. The same is achieved by providing a cushioned mouth guard formed from a plurality of layers of material, wherein the lower jaw and the upper jaw are offset from each other and coupled together with a resilient, yet elastic member.

More specifically, the athletic mouth guard 10 is shown as comprising upper component 12, lower component 14, first and second joining components 16a, 16b and first and second joining cap members 18a, 18b.

Figure 3:
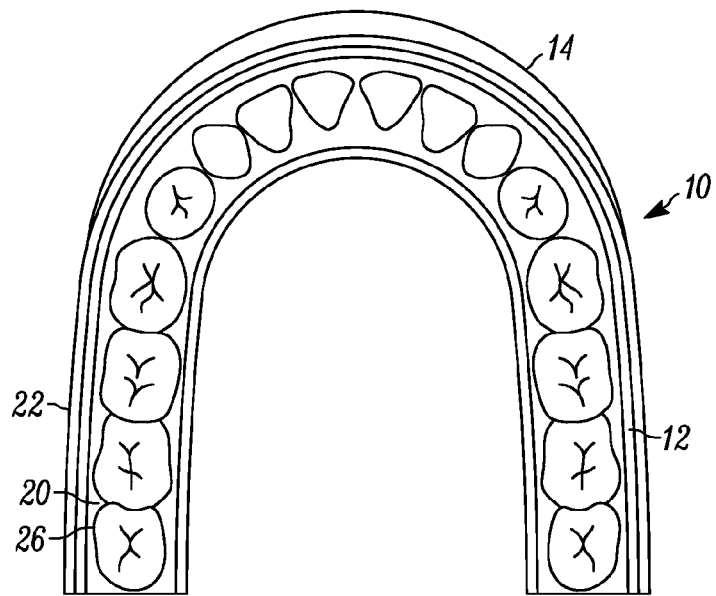
FIG. 3 of the drawings is a top plan view of the athletic mouth guard of the present disclosure.

With continued reference to FIG. 1 and with reference to FIG. 3, the upper component is shown as a molded member which includes an outer surface 22 and an inner surface 20. The upper component is molded so as to define a channel-like configuration so as to surround the teeth in a cup-like fashion so that the inner surface 22 is conformed to substantially abut the teeth and/or gums of a user. Thus, the upper component includes a central region 23 which extends over the incisors and opposing wing regions 25, 27 that extend toward and interact with opposing molars. Preferably, the upper component encases all of the teeth of the user, although, it will be understood that some of the molars may be exposed, as may other teeth. It will be understood that the exact amount of the gums that are encompassed by the device or the amount of surface area contact can be varied without departing from the scope of the disclosure.

The upper component is formed from a plurality of layers, which layers comprise thermoplastic materials. The different layers are typically of different densities and thicknesses to yield an impact absorbing structure. It is contemplated that as few as four layers, and as many as eight layers can be utilized. The various thermoplastic materials comprise most preferably an ethylene vinyl acetate (EVA). Different EVA materials of different thicknesses are available under the tradename Drufosoft from Dentsply Raintree Essix of Sarasota, Fla. One particular combination of layer includes: at least four layers of Drufosoft material in thicknesses that range from 1 mm to 4 mm in thickness. This material, it has been found, provides cushioning to the user and helps to dissipate the results of trauma and contact. In the embodiment shown, the outer layer is clear which allows for the positioning of indicia or logos between the layers. It will be understood that the materials for the layers can be selected for cushioning properties, as well as molding properties (as it is advantageous to mold the inner surface to match the user's teeth and gums).

Figure 4:
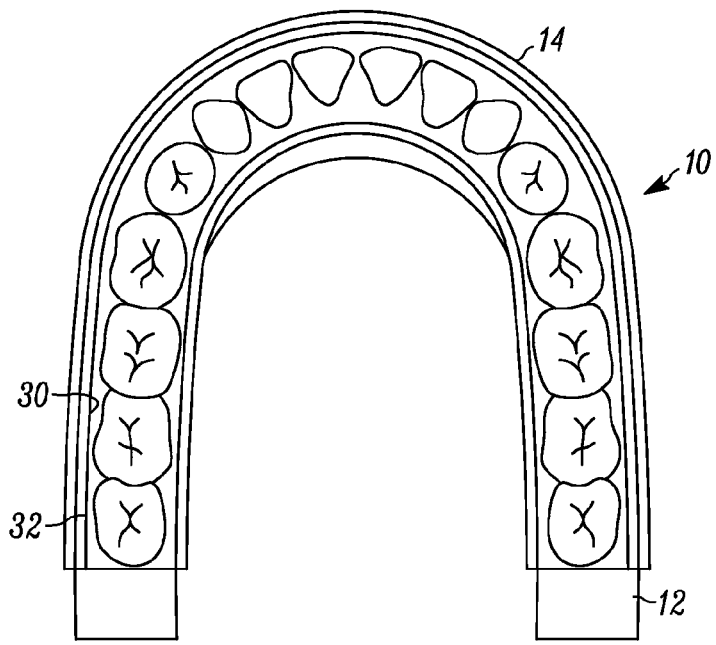
FIG. 4 of the drawings is a bottom plan view of the athletic mouth guard of the present disclosure.

The lower component 14, as is shown in FIGS. 1 and 4, is formed much like the upper component. The lower component is shown as a molded member which includes an outer surface 30 and an inner surface 32. The lower component is molded so as to define a channel-like configuration so as to surround the teeth in a cup-like fashion so that the inner surface 30 is conformed to substantially abut the teeth and/or gums of a user. Thus, the lower component includes a central region 33 which extends over the incisors and opposing wing regions 35, 37 that extend toward and interact with opposing molars. Preferably, the lower component encases all of the teeth of the user, although, it will be understood that some of the molars may be exposed, as may other teeth. It will be understood that the exact amount of the gums that are encompassed by the device or the amount of surface area contact can be varied without departing from the scope of the disclosure.

The lower component is formed from a plurality of layers, which layers comprise thermoplastic materials. The different layers are typically of different densities and thicknesses to yield an impact absorbing structure. It is contemplated that as few as four layers, and as many as eight layers can be utilized. The various thermoplastic materials comprise the same EVA materials set forth above. One particular combination of layer includes: at least four layers of Drufosoft material in thicknesses that range from 1 mm to 4 mm in thickness. This material, it has been found, provides cushioning to the user and helps to dissipate the results of trauma and contact. In the embodiment shown, the outer layer of which is clear, which allows for the positioning of indicia or logos between the layers. It will be understood that the materials for the layers can be selected for cushioning properties, as well as molding properties (as it is advantageous to mold the inner surface to match the user's teeth and gums).

It is contemplated that the coverage of either of the upper component or the lower component may be only partial, with certain teeth being exposed for various reasons. It is contemplated that the broadest range of protection is achieved through coverage of both the upper and lower teeth and matching the same quite closely with adjoining coverage of portions of the gums. However, exposed teeth are contemplated within the scope of the invention.

The joining components 16a, 16b are shown in FIGS. 1, 2, 5 and 6 as extending between the upper component 12 and the lower component 14 along the side regions of each. The joining components 16a, 16b are substantially mirror images of each other. As such, joining component 16a will be discussed with the understanding that joining component 16b is substantially identical.

Figure 2:
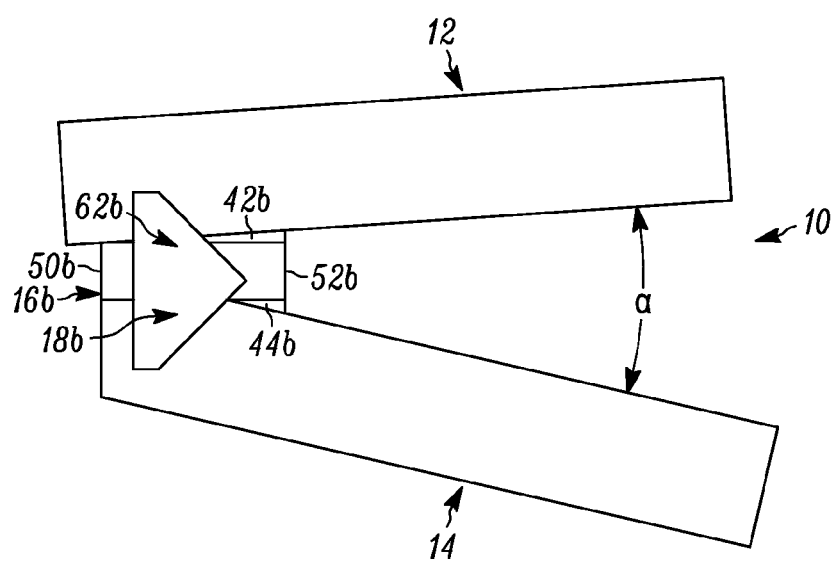
FIG. 2 of the drawings is a side elevational view of the athletic mouth guard of the present disclosure.
Figure 5:
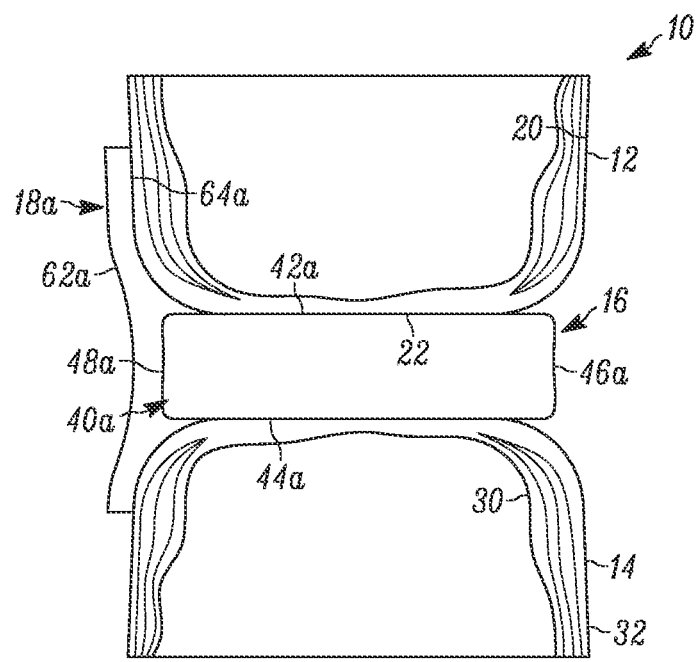
FIG. 5 of the drawings is a partial rear elevational view of the athletic mouth guard of the present disclosure, showing, in particular, the left distal end thereof.

Joining component 16a is shown in FIGS. 1 and 5, as comprising body 40a having upper surface 42a, lower surface 44a, inner end 46a, outer end 48a, proximal end 50a and distal end 52a. The joining component serves to join the upper component 12 to the lower component 14. The upper surface 42a is joined to the outer surface 22 of the upper component along the length thereof. Generally the surface area of the joining extends below a couple of molars of the user, although that distance can be varied (i.e., covering a portion of one of the opposing wings). The lower surface 44a is joined to the outer surface 32 of the lower component 14. As with the upper surface 42a, the lower surface 44a spans a couple of molars of the user. Additionally, the body 40a has a wedge configuration in that it is thicker at the proximal end 50a than it is in the distal end 52a. The wedge configuration, in addition to the length of the body 40a (i.e., the spanning along a plurality of molars), facilitates that angular displacement of the upper component relative to the lower component, at, for example, an angle $\alpha$ (FIG. 2). This angle may be anywhere from 0 degrees (wherein, the lower component and the upper component are substantially parallel to each other) to an angle of, for example, 40 degrees wherein the mouth of the player would be approaching a fully open position. The joining component is made from an elastomeric material which allows the upper component to move relative to the lower component, while maintaining the desired relative angular displacement between the two components, and while maintaining the desired relationship between components.

Figure 6:
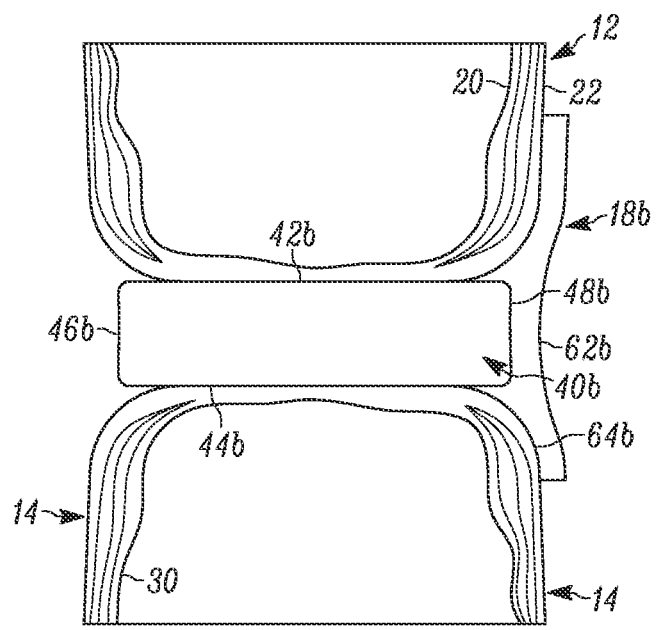
FIG. 6 of the drawings is a partial rear elevational view of the athletic mouth guard of the present disclosure, showing, in particular, the right distal end thereof.

Joining component 16b is shown in FIGS. 1 and 6 as comprising body 40b having upper surface 42b, lower surface 44b, inner end 46b, outer end 48, proximal end 50b and distal end 52b. The joining component 16b, like joining component 16a, serves to join the upper component 12 to the lower component 14. The upper surface 42b is joined to the outer surface 22 of the upper component along the length thereof, in a mirror image to the upper surface 42a of the joining component 16a. Generally the surface area of the joining extends below a couple of molars of the user, although that distance can be varied. The lower surface 44b is joined to the outer surface 32 of the lower component 14. As with the upper surface 42b, the lower surface 44b spans a couple of molars of the user. Additionally, the body 40b has a wedge configuration in that it is thicker at the proximal end 50b than it is in the distal end 52b. The wedge configuration, in addition to the length of the body 40b (i.e., the spanning along a plurality of molars), facilitates that angular displacement of the upper component relative to the lower component. The joining component is made from an elastomeric material which allows the upper component to move relative to the lower component, while maintaining the desired relative angular displacement between the two components, and while maintaining the desired relationship between components.

It will be understood that, in other embodiments, the joining component may comprise a layered structure, or a molded structure which fixes the regions to which it is coupled on each of the upper and lower components to essentially fix the upper and lower components in orientation relative to each other. It is, after all, the relative positioning of the lower and upper teeth and the fixed relationship thereto that, in the end, fosters the proper positioning of the lower jaw in a position forward of the habitual closure of the particular user, and maintains this relationship when the user receives an impact.

The joining cap member 18a and 18b are shown in FIGS. 1, 2, 5 and 6 as being positioned on and attached to opposing outer surfaces of the upper component 12 and lower component 14 covering the outer end 48a, 48b, of the joining components 16a, 16b. Joining cap member 18a includes inner surface 64a and outer surface 62a. Joining cap member 18b includes inner surface 64b and outer surface 62b. The joining cap members are configured to provide additional strength to the joining component to provide increased strength to the joint. In certain embodiments, this component may be eliminated, with the strength of the joint between the joining component and the upper and lower components.

In greater particularity, the joining component is configured and positioned so as to maintain the upper component 12 and the lower component 14 in the desired orientation relative to each other. The desired orientation is one which advances the mandibular (lower) jaw forward relative to the maxillary (upper) jaw and likewise moves the posterior of the tongue forward so that the lower jaw is advanced forward of the habitual closure. The extent of the forward movement is varied for each user, as the same depends on the particular physiology of the user. The relative configuration (i.e., slightly angled) allows for sagittal jaw movement while maintaining the advanced forward position.

Figure 7:
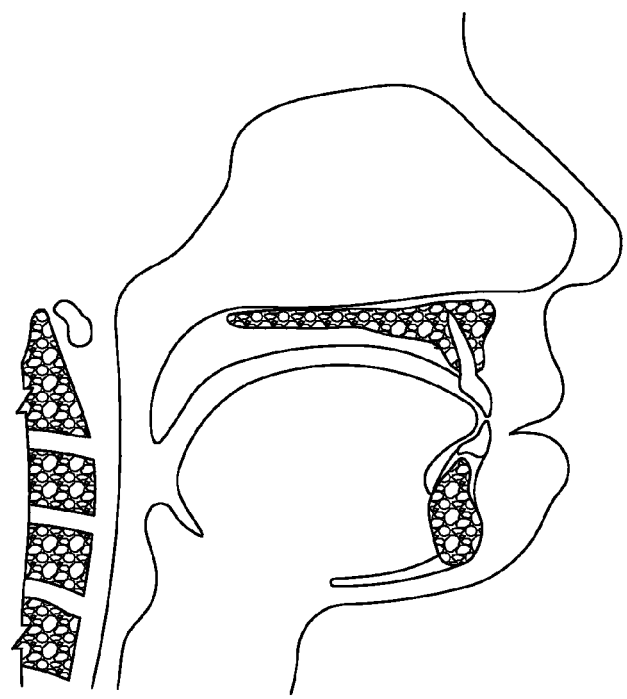
FIG. 7 of the drawings is a cross-sectional depiction of a user whose lower jaw is in the habitual closure position or orientation.
Figure 8:
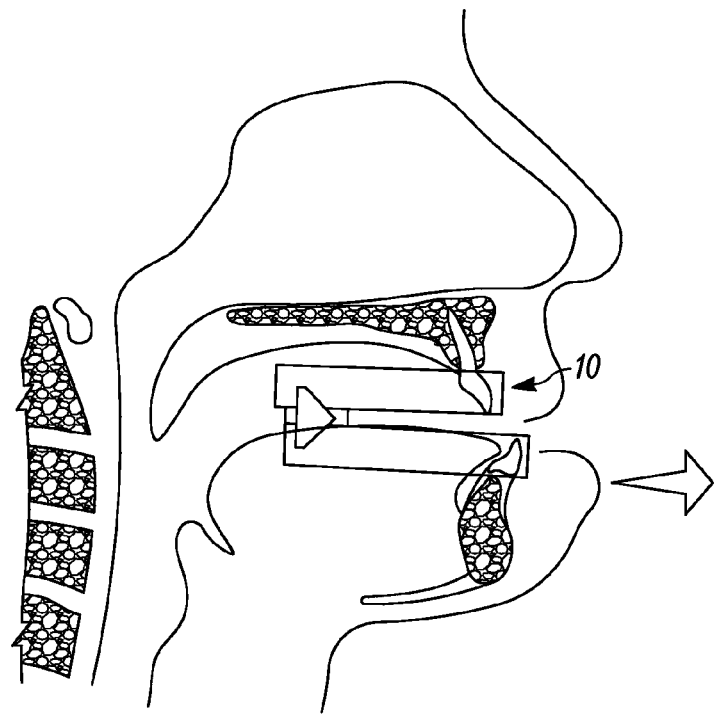
FIG. 8 of the drawings is a cross-sectional depiction of the user of FIG. 7 having the athletic mouth guard of the present disclosure, which has moved the mandibular jaw and the back of the tongue forward beyond the habitual closure position or orientation, into a second forward orientation, thereby opening a larger passageway in the throat and also separating the condyle on either side of the mandibular jaw away from the temporal bone.

With comparative reference to FIGS. 7 and 8, wherein, FIG. 7 shows a cross-section of a head of a user wherein the lower jaw is in habitual closure, and FIG. 8 shows a cross-section of a head of a user wherein the lower jaw is moved forward. The forward advancement of the mandibular jaw alters the temporomandibular joint by separating the condyle on either side of the mandibular jaw away from the temporal bone. This increase in separation greatly reduces the effects of a hit onto the skull and, in turn, the brain. Thus, the chances and the severity of a concussion from a blow to the head is reduced.

At the same time, the forward movement of the mandibular jaw increases the space between the back of the pharanyx and the lower tongue, increasing the size of the air passage of the user. In turn, the user finds breathing easier and finds the increased air flow to the lungs an advantage.

To assemble the device, as each user is different, measurements and the like are likely necessary to custom fit the athletic mouth guard to the user. To measure the user, a professional, such as a dentist or doctor, measures the amount that the user can move the mandibular jaw forward, comfortably, to determine the relative position between the lower component and the upper component. Other measurements such as the depth of the mouth (i.e., how far the teeth extend back), any specific tooth issues, the having or lacking of wisdom teeth, tooth depth, gum line position, etc. Still other measurements as to the comfortable position of the upper and lower jaws when the mouth is open to a desired extent.

With these measurements, the dentist or doctor (or other professional) can provide a blank upper and lower component, as well as fashion the joining component as needed. The bland upper and lower components can be sized to insure coverage over the desired teeth and portions of the gums as desired. Additionally, the upper and lower components can be layered to the extent needed. The more layers, typically, the better the protection. However, the measurements may often dictate the number and thickness of the various layers.

The upper and lower components can be formed in a variety of manners. The separate layers can first be laminated together (i.e., adhered, heat sealed, or otherwise bonded to each other). At such time that they are complete, the joined layers can be first roughly molded in shape to cover the teeth (and portions of the gum if desired) of a typical adult or child user. From there they can be fine tuned. In other embodiments, a plurality of individual layers can be cut into the desired shape and then molded into shape to cover the teeth. The molded individual layers can then be joined together through the processes described. In still other embodiments, a co-molded design is contemplated as well as co-extruded layers that are molded into the desired configuration.

When the upper and lower components are properly sized, they can be heated and introduced into the user's mouth so that the teeth and, where included, the gums make an imprint into the inner surface. Once completed, the components can be quickly cooled so that they maintained the imprinted inner surfaces. Of course, it will be understood that this step can be omitted, however, such a step provides a feeling of a custom fit and can often facilitate the maintenance of the athletic mouth guard in the desired orientation.

Once the upper and lower components are completed, the sizing of the joining components can be determined. That is, the dentist or doctor determines the angle at which to place the upper and lower components and the relative position of the two components so that the mouth guard forces the lower jaw forward. It is the joining component that maintains this relative relationship in the desired position. The joining component is fashioned and dimensioned so as to maintain the desired position of the lower and upper components. And, once formed, it is coupled (i.e., adhered, laminated or heat sealed, fastened or otherwise joined) to the outer surfaces of the upper and lower components.

At this point the upper and lower components are joined to each other and have a relative position with respect to each other. However, as the elements are elastomeric, they have the ability to flex. Thus, each component can elastically flex to a certain extent relative to the other components.

Inasmuch as the joining component has a substantial amount of stress incurred through the lower jaw trying to return to its habitual configuration and placement, as well as the stresses associated with biting, merely moving the lower jaw or being hit, each joining cap member 18a, 18b is coupled (i.e., adhered, laminated or heat sealed, fastened or otherwise joined) to the upper component, the lower component and the joining component so as to provide an additional surface area of attachment to those components, and to reduce the stress on the joint between the joining component and the upper component as well as the joining component and the lower component.

In use, the user places the device into his or her mouth. By fitting the teeth into the desired location the user's lower jaw is directed forward and as is the lower back of the tongue. The movement is such that the lower jaw is directed forward of the habitual closure. And, the tongue is similarly moved forward. In turn, the user can breathe better, as the passageway between the pharynx and the back of the tongue is naturally enlarged. Second, the temporomandibular joint is altered by separating the condyle on either side of the mandibular jaw away from the temporal bone.

Thus, when the user is hit, the laminated layers of material serve to cushion the impact and to dissipate force. This, in turn, slows down the movement of the lower jaw in the process of an impact—thereby lessening the impact that can be transferred to the skull. Additionally, the separation of the condyle from the temporal bone lessens the impact that is directed through the lower jaw into the skull. In many sports, the lower chin strap tends to do the exact opposite, and tends to make impacts more severe. With the present mouth guard, the impact is lessened even with the use of a chin strap.

Thus, in the end, the user is able to breathe better and is likewise better protected from concussions. Advantageously, the mouth guard also protects the user's teeth and tongue from damage, much like a typical mouth guard. Thus, the additional features of the mouth guard do not negatively impact other benefits, such as the benefits of conventional mouth guards.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. An athletic mouth guard comprising:
    an upper component having a central region and first and second opposing wing regions to define a channel-like configuration which is structurally configured to receive a plurality of teeth of an upper jaw of a user;
    a lower component having a central region and first and second opposing wing regions to define a channel-like configuration which is structurally configured to receive a plurality of teeth of a lower jaw of a user;
    a first joining component which is attached to the upper component and to the lower component along corresponding first opposing wing regions of the upper and lower components, and a second joining component which is attached to the upper component and to the lower component along corresponding second opposing wing regions of the upper and lower components so as to fix the portions of the wing regions to the respective first and second joining component, and to each other, the first and second joining components coupling the upper component and the lower component, in a spaced apart orientation, such that placement of the same in a mouth of a user directs a lower jaw of a mouth of a user to move forward relative to a position thereof in a habitual closure;
    a first joining cap member extending over and attached to a portion of the upper component, the lower component and the first joining component, to, in turn, provide enhanced strength thereto; and
    a second joining cap member extending over and attached to a portion of the upper component, lower component and the second joining component, to, in turn, provide enhanced strength thereto.

2. The athletic mouth guard of claim 1 wherein the upper component comprises a plurality of layers of elastically deformable thermoplastic material.

3. The athletic mouth guard of claim 2 wherein the plurality of layers comprises at least four layers.

4. The athletic mouth guard of claim 2 wherein the lower component comprises a plurality of layers of elastically deformable thermoplastic material.

5. The athletic mouth guard of claim 1 wherein the upper component and the lower component are one of substantially parallel to each other, and, angled relative to each other so as to increasingly separate away from the first and second joining components.

6. The athletic mouth guard of claim 5 wherein the upper component and the lower component are angled relative to each other at an angle α, which is greater than 0 degrees and less than or equal to 40 degrees.

7. The athletic mouth guard of claim 1 wherein the upper and the lower components include four layers each, which layers include EVA.

8. A method of participating in a contact sport comprising the steps of:

providing an athletic mouth guard to a participant of a contact sport having:

an upper component having a central region and first and second opposing wing regions to define a channel-like configuration which is structurally configured to receive a plurality of teeth of an upper jaw of the participant;

a lower component having a central region and first and second opposing wing regions to define a channel-like configuration which is structurally configured to receive a plurality of teeth of a lower jaw of the participant; and a first joining component which is attached to the upper component and to the lower component along corresponding first opposing wing regions of the upper and lower components, and a second joining component which is attached to the upper component and to the lower component along corresponding second opposing wing regions of the upper and lower components so as to fix the portions of the wing regions to the respective first and second joining component, and to each other, the first and second joining components coupling the upper component and the lower component in a spaced apart orientation, such that placement of the same in a mouth of a user directs a lower jaw of a mouth of a participant to move forward relative to a position thereof in a habitual closure;

placing the athletic mouth guard into the participant;

moving the lower jaw of the participant forward relative to the upper jaw and relative to the position of the lower jaw in the habitual closure of the participant;

moving the tongue of the participant forward relative to the position of tongue in the habitual closure of the participant, to, in turn, enlarge an airway passage of the participant; and participating in the contact sport, wherein the position of the lower jaw relative to the upper jaw and the forwarded position of the tongue is substantially maintained.

9. The method of claim 8 wherein the athletic mouth guard further includes a first joining cap member extending over and attached to a portion of the upper component, the lower component and the first joining component, to, in turn, provide enhanced strength thereto, and a second joining cap member extending over and attached to a portion of the upper component, lower component and the second joining component, to, in turn, provide enhanced strength thereto.

10. The method of claim 8 wherein the upper component of the athletic mouth guard comprises a plurality of layers of elastically deformable thermoplastic material.

11. The method of claim 8 wherein the lower component of the athletic mouth guard comprises a plurality of layers of elastically deformable thermoplastic material.

12. The method of claim 8 wherein the upper component and the lower component of the athletic mouth guard are one of substantially parallel to each other, and, angled relative to each other so as to increasingly separate away from the first and second joining components.

* * * * *